(12) United States Patent
Lin et al.

(10) Patent No.: US 6,408,694 B1
(45) Date of Patent: Jun. 25, 2002

(54) APPARATUS AND METHOD FOR ON-LINE MONITORING OF A LIQUID DENSITY

(75) Inventors: Chun Chih Lin, Taipei; Lung-Chun Tsai; Ching Fang Kam, both of Hsin-Chu; Han-Chang Lee, Taoyuan, all of (TW)

(73) Assignee: Taiwan Semiconductor Manufacturing Company, Ltd., Hsin Chu (TW)

( * ) Notice: Subject to any disclaimer, the term of this patent is extended or adjusted under 35 U.S.C. 154(b) by 0 days.

(21) Appl. No.: 09/451,239

(22) Filed: Nov. 29, 1999

(51) Int. Cl.$^7$ ................................................ G01N 9/18
(52) U.S. Cl. ......................................... 73/444; 73/445
(58) Field of Search .......................... 73/444, 445, 448, 73/453, 32 R

(56) References Cited

U.S. PATENT DOCUMENTS

| | | | | |
|---|---|---|---|---|
| 756,702 A | * | 4/1904 | Porter | 73/444 |
| 1,709,139 A | * | 4/1929 | Manchester et al. | 73/445 |
| 3,952,761 A | * | 4/1976 | Friedland | 73/445 |
| 4,400,978 A | * | 8/1983 | Guay et al. | 73/453 |

\* cited by examiner

*Primary Examiner*—John E. Chapman
(74) *Attorney, Agent, or Firm*—Tung & Associates

(57) ABSTRACT

An apparatus and a method for on-line, real-time monitoring of a liquid density in a chemical process are provided. The apparatus is constructed by an upright, cylindrical housing that has a cavity defined therein for holding a liquid, and a density indicator mounted inside the cavity and positioned by at least two positioning guides which are fixedly attached to the housing wall. The apparatus may further include a stabilizing plate positioned at the bottom portion of the cylindrical housing for flowing a liquid in a downward direction such that the liquid flow does not cause a turbulent in the cavity so as to improve the stability and accuracy of the liquid density reading. The liquid density can be read either manually by a measuring stick on the density indicator against a graduated scale marked on the cylinder wall, or by optical sensors automatically which are connected to a process controller or an alarm panel to alert an operator or to stop the process machine when the liquid density falls outside of an allowable range.

19 Claims, 2 Drawing Sheets

APPARATUS AND METHOD FOR ON-LINE MONITORING OF A LIQUID DENSITY

FIELD OF THE INVENTION

The present invention generally relates to an apparatus and a method for on-line monitoring of a liquid density and more particularly, relates to an apparatus and a method for on-line, real-time monitoring of a liquid density by a densimeter cylinder that contains a density indicator therein for the continuous monitoring of density by flowing the liquid continuously through the densimeter cylinder.

BACKGROUND OF THE INVENTION

In the fabrication process for semiconductor devices, a pre-processed semiconductor wafer is frequently polished in order to planarize a top surface of the wafer or to remove excess materials from the surface of the wafer. While apparatus for polishing semiconductor wafers is well known in the art, a chemical-mechanical polishing method has been developed for specific applications on silicon wafers. The chemical-mechanical polishing (CMP) method is named as such because both a chemical reaction between a polishing slurry and a polished surface and a mechanical reaction for removing the debris are involved in the CMP process.

More recently, chemical-mechanical polishing apparatus has been employed in combination with a pneumatically actuated polishing head. CMP apparatus is used primarily for polishing the front surface or the device-side of a semiconductor wafer during the fabrication of semiconductor devices on the wafer. A wafer is planarized or smoothed one or more times during a fabrication process in order for the top surface of the wafer to be as flat as possible. A wafer is polished by being placed on a carrier and pressed face down onto a polishing pad covered with a slurry of colloidal silica or alumina in de-ionized water.

A cross-sectional view of a CMP apparatus is shown in FIGS. 1A and 1B. As shown in FIG. 1A, a rotating polishing head 14 which holds a wafer, 10 is pressed onto an oppositely rotating polishing pad 12 mounted on a polishing disc 26 by adhesive means. The polishing pad 12 is pressed against the wafer surface 22 at a predetermined pressure. During polishing, a slurry 24 is dispensed in droplets onto the surface of the polishing pad 12 to effectuate the chemical mechanical removal of materials from the wafer surface 22.

An enlarged cross-sectional representation of the polishing action which results from a combination of chemical and mechanical effects is shown in FIG. 1B. The CMP method can be used to provide a planner surface on dielectric layers, on deep and shallow trenches that are filled with polysilicon or oxide, and on various metal films. A possible mechanism for the CMP process involves the formation of a chemically altered layer at the surface of the material being polished. The layer is mechanically removed from the underlying bulk material. An outer layer is then regrown on the surface while the process is repeated again. For instance, in metal polishing, a metal oxide layer can be formed and removed repeatedly.

During a CMP process, a large volume of a slurry composition is dispensed. The slurry composition and the pressure applied between the wafer surface and the polishing pad determine the rate of polishing or material removal from the wafer surface. The chemistry of the slurry composition plays an important role in the polishing rate of the CMP process. For instance, when polishing oxide films, the rate of removal is twice as fast in a slurry that has a pH of 11 than with a slurry that has a pH of 7. The hardness of the polishing particles contained in the slurry composition should be about the same as the hardness of the film to be removed to avoid damaging the film. A slurry composition typically consists of an abrasive component, i.e., has particles and components that chemically react with the surface of the substrate. For instance, a typical oxide polishing slurry composition consists of a colloidal suspension of oxide particles with an average size of 30 nm suspended in an alkali solution at a pH larger than 10. A polishing rate of about 120 nm/min can be achieved by using this slurry composition. Other abrasive components such as ceria suspensions may also be used for glass polishing where large amounts of silicon oxide must be removed. Ceria suspensions act as both the mechanical and the chemical agent in the slurry for achieving high polishing rates, i.e., larger than 500 nm/min. While ceria particles in the slurry composition remove silicon oxide at a higher rate than do silica, silica is still preferred because smoother surfaces can be produced. Other abrasive components, such as alumina ($Al_2O_3$) may also be used in the slurry composition.

Since the concentration of particles in the slurry solution plays an important role in the CMP process, it must be carefully monitored before it is dispensed onto the surface of a wafer for performing the CMP process. Conventionally, the density, or the specific gravity of a slurry solution can be determined on a batch basis by a standard densimeter. Samples must be regularly taken from a slurry supply tank and tested for its density to insure it falls within a permissible range. This is a laborious and time consuming process, and is subjected to high probability of human errors. A conventional densimeter 30 is shown in FIG. 1C. The densimeter is constructed by an upright, elongated cylinder 32 fabricated of a substantially transparent material. The cylinder is mounted on a base plate 34 for stability and for forming a fluid-tight container. Inside a cavity 36 of the cylinder 32, a density indicator 40 is provided and submerged in a liquid 38. The density indicator 40 is constructed by a floater portion 42 and a measuring stick 44 which are integrally joined together. The floater portion 42 is constructed of a material that is suitable for the density of the liquid 38 to be measured such that it suspends in the liquid as shown in FIG. 1C. The density of the liquid 38 in the cavity 36 can be read by the position of the marker 46 on the measuring stick relative to the graduated scale 48 on the cylinder wall 50. The process does not allow an on-line, real-time monitoring of liquid density.

Another device which utilizes ultrasonic waves sent through a liquid medium has also been used to measure density of a liquid. The device is very expensive and the technique is operator sensitive and subjected to a number of material parameters which may lead to inaccurate readings. For instance, when the liquid material contains air bubbles, the density reading obtained by the ultrasonic method may be greatly affected. Furthermore, due to the high cost of the ultrasonic equipment, the on-line density measurement technique cannot be used at all fabrication facilities. Moreover, the equipment is a complicated electronic device that requires an elaborate calibration procedure which must be flawlessly performed in order to obtain accurate results.

It is therefore an object of the present invention to provide an apparatus for on-line monitoring a liquid density that does not have the drawbacks or shortcomings of the conventional apparatus.

It is another object of the present invention to provide an apparatus for on-line monitoring of a liquid density that can be used for the continuous monitoring of a liquid density used in a chemical process.

It is a further object of the present invention to provide an apparatus for on-line monitoring of a liquid density which can be carried out on a real-time basis in a chemical process.

It is another further object of the present invention to provide an apparatus for on-line monitoring of a liquid density by utilizing a density indicator situated in a cylindrical-shaped housing for a liquid to flow therethrough continuously such that a real-time monitoring of the liquid density can be obtained.

It is still another object of the present invention to provide an apparatus for on-line monitoring of a liquid density by utilizing an upright, cylindrical housing for flowing a liquid therethrough equipped with a density indicator and positioning guides for holding the indicator in an upright position.

It is yet another object of the present invention to provide an apparatus for on-line monitoring of a liquid density which is equipped with optical sensing means for alerting a machine operator when the liquid density measured is out of specification.

It is still another further object of the present invention to provide a method for on-line monitoring of a liquid density in a chemical process by flowing a liquid through an upright, cylindrical-shaped housing equipped with a density indicator therein for the real-time monitoring of the liquid density.

It is yet another further object of the present invention to provide a method for on-line, real-time monitoring of a liquid density in a chemical process on a continuous basis which includes the use of an automatic detection apparatus which alerts a machine operator of an out of specification density measured.

SUMMARY OF THE INVENTION

In accordance with the present invention, an apparatus and a method for on-line, real-time monitoring of a liquid density in a chemical process are provided.

In a preferred embodiment, an apparatus for on-line monitoring of a liquid density can be provided which includes an upright, cylindrical housing that is substantially transparent and fluid-tight defining a cavity therein, a liquid inlet tube in fluid communication with a lower portion of the cavity, a liquid outlet tube in fluid communication with a middle portion of the cavity, a quantity of liquid in the cavity which has a top surface substantially at the same elevation of the liquid outlet tube, a density indicator constructed of a float and a measuring stick integrally joined together such that when the float is submerged in the liquid, the measuring stick is emerged above the top level of the liquid, and at least two positioning guides fixedly attached to the cylindrical housing adapted for guiding the measuring stick in a substantially upright position.

In the apparatus for on-line monitoring of a liquid density, the cylindrical housing may further include a graduated scale marked thereon for determining the relative position of the measuring stick when the float is submerged in a liquid. The apparatus may further include a stabilizing plate positioned at the lower portion of the cavity in the housing with the liquid inlet tube connected therethrough for feeding a liquid downwardly toward a bottom of the cylindrical housing, the stabilizing plate partially separates the lower portion of the cavity from the cavity. The apparatus may further include a sensing device for sensing the position of the measuring stick and for sending out a signal to a process controller on a process machine which consumes the liquid.

In the apparatus for on-line monitoring of a liquid density, the sensing device may include a pair of optical sensors for sensing a predetermined point on the measuring stick inbetween a high density mark and a low density mark. Each of the optical sensors may include an optical beam sender and an optical beam receiver. The quantity of liquid in the cavity may be a slurry solution used in a chemical mechanical polishing process. The apparatus may further include a flow regulating device in the liquid inlet tube for adjusting a flow rate of the liquid flowing through the inlet tube. The at least two positioning guides each has an eyelet for slidingly engaging the measuring stick therethrough.

The present invention is further directed to a method for on-line measuring a liquid density in a chemical process which can be carried out by the operating steps of providing an upright, cylindrical housing in a substantially transparent material defining a fluid cavity therein, connecting a liquid inlet tube in fluid communication with a lower portion of the cavity partially separated from the cavity by a stabilizing plate, connecting a liquid outlet tube in fluid communication with a middle portion of the cavity, positioning a density indicator in the cavity, the density indicator includes a float portion and a measuring stick integrally joined together such that the float portion submerges in a liquid while the measuring stick portion emerges above a liquid level when a liquid is filled in the cavity, mounting at least two positioning guides to an inside wall of the cylindrical housing for sliding engagement with the measuring stick, filling the cavity with the liquid through the liquid inlet tube until a liquid level is maintained substantially at the liquid outlet tube, and reading a density of the liquid from a relative position of the measuring stick of the density indicator.

The method for on-line measuring a liquid density in a chemical process may further include the step of marking a graduated scale on the upright, cylindrical housing for reading a density. The method may further include the steps of mounting a sensing device on the upright, cylindrical housing, and sensing a position of the measuring stick.

In the method for on-line measuring a liquid density in a chemical process, the sensing device may be a pair of optical sensors for sensing a maximum allowable and a minimum allowable density. The method may further include the step of sending an alarm signal to a process controller when the liquid density measured is outside a range between the maximum allowable density and the minimum allowable density. Each of the pair of optical sensors may include an optical beam sender and an optical beam receiver. The method may further include the step of flowing the liquid into the lower portion of the cavity partially partitioned by the stabilizing plate without causing a turbulent flow in the cavity.

In another preferred embodiment, an apparatus for on-line, real-time monitoring a liquid density can be provided which includes a transparent, fluid-tight, cylindrical-shaped housing in an upright position, a cavity for holding a liquid defined by the cylindrical-shaped housing, a liquid inlet tube in fluid communication with a lower portion of the cavity, a liquid outlet tube in fluid communication with a middle portion of the cavity, a quantity of liquid in the cavity which has a top level substantially at the same elevation as the liquid outlet tube, a density indicator constructed of a float and a measuring stick integrally joined together such that when the float is submerged in the liquid, the measuring stick is emerged above the top level of the liquid, at least two positioning guides fixedly attached to the cylindrical housing adapted for guiding the measuring stick in a substantially upright position, and an optical sensor mounted on the cylindrical-shaped housing for sensing a position of the measuring stick.

The apparatus for on-line, real-time monitoring of a liquid density may further include a process controller for receiving a signal indicative of a density reading from the optical sensor and comparing the signal to a pre-set density value. The optical sensor may include two pairs of optical beam senders and optical beam receivers for sensing a maximum allowable density value and a minimum allowable density value. The apparatus may further include a process controller which stops a chemical process when the density reading obtained by the controller is outside an allowable range of the pre-set density values.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

Figure 1A:
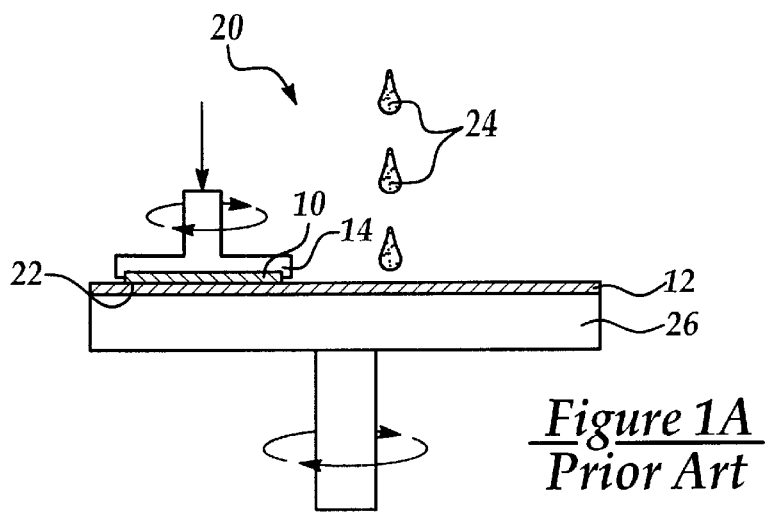
FIG. 1A is a simplified illustration of a cross-sectional view of a chemical mechanical polishing apparatus.
Figure 1B:
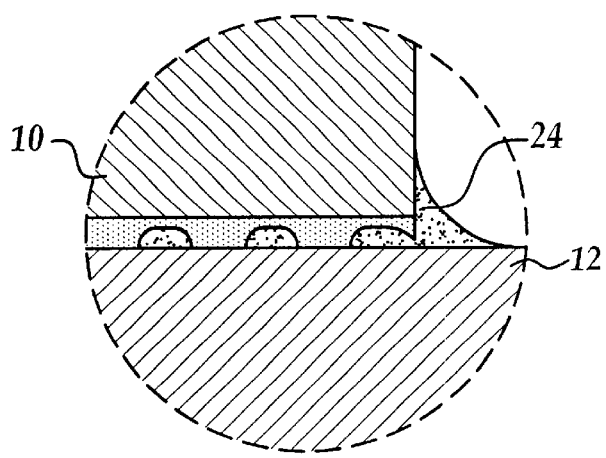
FIG. 1B is an enlarged, cross-sectional view of the CMP apparatus of FIG. 1A showing the interaction between the slurry and the wafer surface polished.
Figure 1C:
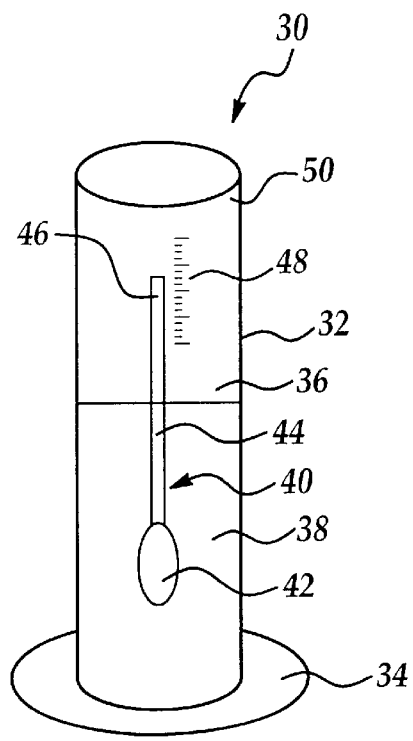
FIG. 1C is a perspective view of a conventional densimeter used in measuring density of a liquid on a batch basis.

The present invention discloses an apparatus for the on-line, real-time monitoring of a liquid density used in a chemical process and more particularly, used in a semiconductor fabrication process. While the on-line monitoring of a slurry solution used in a chemical-mechanical polishing process is used as an illustration here, the present invention novel apparatus and method is in no way limited to such applications. As long as a suitable density indicator of the floating type can be selected to suit a specific range of liquid densities, the present invention novel apparatus can be used for measuring any liquid density used in any chemical processes.

In a preferred embodiment, the apparatus for on-line, real-time monitoring of a liquid density can be provided in an upright, cylindrical housing that is fabricated of a substantially transparent material defining a cavity therein for holding a quantity of liquid in the cavity, a density indicator submerged in the liquid, and at least two positioning guides for guiding the density indicator. The cylindrical housing is further equipped with a liquid inlet tube that is in fluid communication with a lower portion of the cavity and a liquid outlet tube that is in fluid communication with a middle portion of the cavity. The quantity of liquid in the cavity has a top fluid level that is substantially at the same elevation as the liquid outlet tube. The cylindrical housing is further equipped with a graduated scale marked on the housing for determining the relative position of the density indicator, or the relative position of a measuring stick of the density indicator. The cylindrical housing is further equipped with a stabilizing plate partially separating a lower portion of the cavity from the upper portion of the cavity for the liquid inlet tube to go therethrough such that liquid flows through the inlet tube toward the bottom of the cylindrical housing without causing a turbulent flow of liquid in the cavity.

The present invention further provides a method for on-line measuring a liquid density in a chemical process by first providing an upright, cylindrical housing in a substantially transparent material that defines a fluid cavity therein, connecting a liquid inlet tube in fluid communication with the lower portion of the cavity which is partially separated from the cavity by a stabilizing plate, and connecting a liquid outlet tube in fluid communication with a middle portion of the cavity. A density indicator is then provided in the cavity which includes a float portion and a measuring stick that is integrally joined with the float portion such that when the float portion submerges in a liquid, the measuring stick emerges above the liquid level when the cavity is filled with a liquid. At least two positioning guides are mounted to the inside wall of the cylindrical housing for sliding engagement with the measuring stick. After the cavity is filled with a liquid through the liquid inlet tube until a level is maintained substantially at the liquid outlet tube, a density of the liquid can be read from a relative position of the measuring stick of the density indicator by the graduated scale marked on the cylindrical cylinder. The method may further include the steps of mounting a sensing device such as an optical sensor on the cylindrical housing and then sensing a position of the measuring stick and thus obtaining a density measurement automatically by the optical sensor. The optical sensor may further send an alarm signal to a process controller when the liquid density sensed is outside a range between a maximum and a minimum allowable density.

The present invention novel apparatus and method therefore allows the on-line, real-time monitoring of a liquid density in a chemical process on a continuous basis. Such is not possible with any of the conventional apparatus and method.

Figure 2:
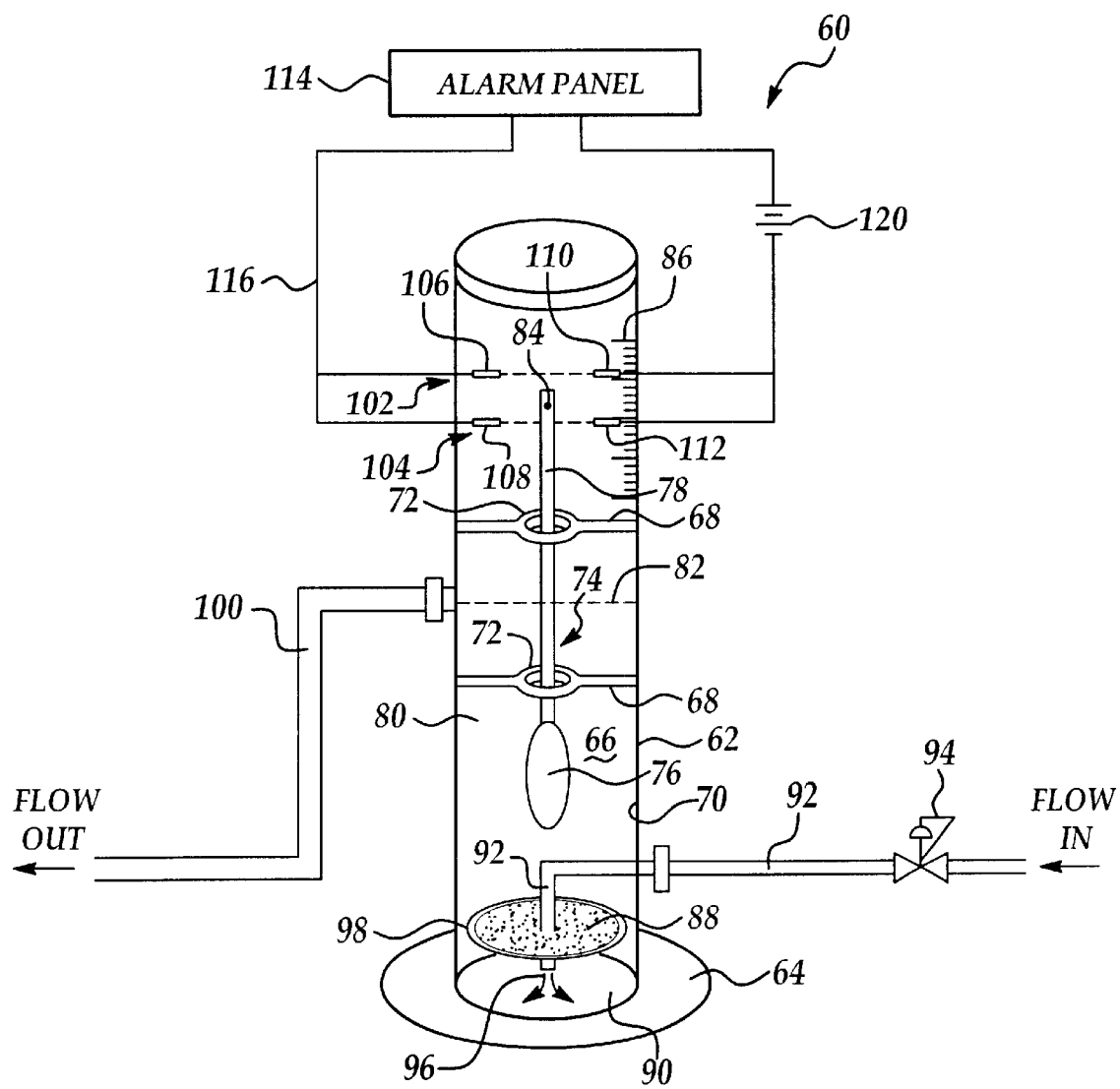
FIG. 2 is a perspective view of the present invention apparatus for on-line, real-time monitoring of a liquid density.

Referring now to FIG. 2 wherein a present invention apparatus 60 for the on-line detection of a liquid density is shown. The apparatus 60 is constructed of an upright, elongated cylindrical-shaped housing 62 which is fabricated of a substantially transparent material of either plastic or glass. The elongated cylindrical-shaped housing 62 is stabilized and sealed on the bottom end by a base plate 64 to form a fluid-tight container and a cavity 66 therein. Inside the cavity 66, at least two positioning guides 68 are fixedly attached to the inside wall 70 of the housing 62. The positioning guide 68 each having an eyelet 72 at a center for guiding a density indicator 74 therein. The density indicator 74 is constructed of a float portion 76 and a measuring stick 78 which are integrally joined together. The float portion 76 of the density indicator can be fabricated in a suitable material for the specific application of the liquid 80 that fills the cavity 66. For different liquid materials, different types of float portion 76 is required such that it produces adequate buoyancy for the measuring stick 78 to emerge above the liquid level 82. As shown in FIG. 2, the measuring stick 78 is guided through the eyelets 72 of the positioning guide 68 such that it slides in an up and down motion to indicate the liquid density by a marker 84 on the measuring stick 78. A graduated scale 86 is marked on the cylindrical housing 62 for such purpose. Different types of density indicator 74 can be commercially obtained from suppliers for indicating specific ranges of liquid densities.

Inside the cylindrical-shaped housing 62, is further provided a stabilizing plate 88 to partially separate a lower portion 90 of the cavity from the main portion of cavity 66. The stabilizing plate 88 can be suitably positioned and supported by an inlet tube 92 which also goes through the cylinder wall 62. The liquid inlet tube 92 is further provided with a flow regulator 94 for regulating a liquid flow through the tube. As shown in FIG. 2, liquid 96 enters the lower cavity portion 90 in a downward direction and then enters the main cavity 66 through a gap 98 formed between the stabilizing plate 88 and the sidewall 70 of the cylindrical housing 62. This is an important aspect of the present invention novel apparatus since it prevents the formation of a turbulent flow in the cavity 66 and therefore, improves the accuracy of the density reading by stabilizing the density indicator 74.

The present invention novel apparatus allows a continuous, on-line monitoring of a liquid density by flowing a liquid continuously out of the liquid outlet tube 100 mounted at the top liquid level 82 in the cylindrical housing 62. A continuous steady flow of liquid through the inlet 92, the lower chamber cavity 90, the upper chamber cavity 66 and the liquid outlet tube 100 enables a continuous, on-line and real-time monitoring of the liquid density to be made by visually reading the position of marker 84 relative to the graduated scale 86 on the cylindrical housing 62.

Other than the manual reading method described above, the present invention novel apparatus can be completely automated by mounting sensors on the cylindrical housing 62. As shown in FIG. 2, optical sensors 102, 104 are mounted on the cylindrical housing 70 for such purpose. Each of the optical sensors 102, 104 consists of optical beam senders 106, 108 and optical beam receivers 110, 112. The optical sensor 102, which consists of optical beam sender 106 and optical beam receiver 110, detects a maximum allowable density, while the optical sensor 104 which consists of optical beam sender 108 and optical beam receiver 112, detects the minimum liquid density by detecting the marker 84 on the measuring stick 78. For instance, for an oxide slurry solution that is frequently used in a CMP process, the liquid density of the slurry has an allowable range between 1.068 gm/cc and 1.076 gm/cc. The optical beam receiver 110 can therefore be set at 1.076 gm/cc, i.e., at the maximum allowable density, while the optical beam receiver 112 can be set at 1.068 gm/cc, i.e., at the lowest allowable density. When the marker 84 on the measuring stick 78 exceeds the maximum or the minimum density values, a signal is sent to the alarm panel 114 through wiring 116 to alert the machine operator. The signal may further be sent to a process controller for automatically shutting down the polishing apparatus. The optical sensors 102, 104 may be powered by a power supply 120. In an oxide slurry commonly used for the CMP process, the solid: DI water ratio may be 62 parts:70 parts.

The present invention novel apparatus and method for the on-line, real-time monitoring of a liquid density on a continuous basis have therefore been amply described in the above descriptions and in the appended drawing of FIG. 2.

While the present invention has been described in an illustrative manner, it should be understood that the terminology used is intended to be in a nature of words of description rather than of limitation.

Furthermore, while the present invention has been described in terms of a preferred and alternate embodiment, it is to be appreciated that those skilled in the art will readily apply these teachings to other possible variations of the inventions.

The embodiment of the invention in which an exclusive property or privilege is claimed are defined as follows:

What is claimed is:

1. An apparatus for on-line monitoring of a liquid density comprising:
    an upright, cylindrical housing that is substantially transparent and fluid-tight defining a cavity therein,
    a liquid inlet tube in fluid communication with a lower portion of said cavity,
    a liquid outlet tube in fluid communication with a middle portion of said cavity,
    a stabilizing plate positioned at said lower portion of said cavity in said housing with said liquid inlet tube connected therethrough for feeding a liquid downwardly toward a bottom of said cylindrical housing, said stabilizing plate partially separates said lower portion of cavity from said cavity,
    a quantity of liquid in said cavity having a top level substantially at the same elevation of said liquid outlet tube,
    a density indicator constructed of a float and a measuring stick integrally joined together such that when the float is submerged in said liquid, the measuring stick is emerged above said top level of the liquid, and
    at least two positioning guides fixedly attached to said cylindrical housing adapted for guiding said measuring stick in a substantially upright position.

2. An apparatus for on-line monitoring of a liquid density according to claim 1, wherein said cylindrical housing further comprises a graduated scale marked thereon for determining the relative position of said measuring stick when said float is submerged in a liquid.

3. An apparatus for on-line monitoring of a liquid density according to claim 1 further comprising a sensing device for sensing the position of said measuring stick and for sending out a signal to a process controller on a process machine which consumes said liquid.

4. An apparatus for on-line monitoring of a liquid density according to claim 3, wherein said sensing device comprising a pair of optical sensors for sensing a predetermined marker on said measuring stick inbetween a high density mark and a low density mark.

5. An apparatus for on-line monitoring of a liquid density according to claim 4, wherein each of said optical sensors comprises an optical beam sender and an optical beam receiver.

6. An apparatus for on-line monitoring of a liquid density according to claim 1, wherein said quantity of liquid in said cavity being a slurry solution used in a chemical mechanical polishing process.

7. An apparatus for on-line monitoring of a liquid density according to claim 1 further comprising a flow regulating device in said liquid inlet tube for adjusting a flow rate of said liquid through said inlet tube.

8. An apparatus for on line monitoring of a liquid density according to claim 1, wherein said at least two positioning guides each comprises an eyelet for slidingly engaging said measuring stick therethrough.

9. A method for on-line measuring a liquid density in a chemical process comprising the steps of:
    providing an upright, cylindrical housing in a substantially transparent material defining a cavity therein,
    connecting a liquid inlet tube in fluid communication with a lower portion of said cavity partially separated from said cavity by a stabilizing plate,
    connecting a liquid outlet tube in fluid communication with a middle portion of said cavity,
    positioning a density indicator in said cavity, said density indicator comprises a float portion and a measuring stick integrally joined together such that the float portion submerges in a liquid while said measuring stick emerges above a liquid level when a liquid is filled in said cavity,
    mounting at least two positioning guides to an inside wall of said cylindrical housing for sliding engagement with said measuring stick, filling said cavity with said liquid through said liquid inlet tube until a liquid level is maintained substantially at said liquid outlet tube, and reading a density of said liquid from a relative position of said measuring stick of said density indicator.

10. A method for on-line measuring a liquid density in a chemical process according to claim 9 further comprising the step of marking a graduated scale on said upright, cylindrical housing for reading a density.

11. A method for on-line measuring a liquid density in a chemical process according to claim 9 further comprising the steps of:

mounting a sensing device on said upright, cylindrical housing, and sensing a position of a predetermined marker on said measuring stick.

12. A method for on-line measuring a liquid density in a chemical process according to claim 11, wherein said sensing device being a pair of optical sensors for sensing a maximum allowable and a minimum allowable density.

13. A method for on-line measuring a liquid density in a chemical process according to claim 12 further comprising the step of sending an alarm signal to a process controller when said liquid density measured is outside a range between said maximum allowable density and said minimum allowable density.

14. A method for on-line measuring a liquid density in a chemical process according to claim 12, wherein each of said pair of optical sensors comprises an optical beam sender and an optical beam receiver.

15. A method for on-line measuring a liquid density in a chemical process according to claim 9 further comprising the step of flowing said liquid into said lower portion of cavity partially partitioned by said stabilizing plate without causing a turbulent flow in said cavity.

16. An apparatus for on-line, real-time monitoring of a liquid density comprising:

a transparent, fluid-tight, cylindrical-shaped housing in an upright position, a cavity for holding a liquid defined by said cylindrical-shaped housing, a liquid inlet tube in fluid communication with a lower portion of said cavity, a liquid outlet tube in fluid communication with a middle portion of said cavity, a stabilizing plate positioned at said lower portion of said cavity in said housing with said liquid inlet tube connected therethrough for feeding a liquid downwardly toward a bottom of said cylindrical housing, said stabilizing plate partially separates said lower portion of cavity from said cavity, a quantity of liquid in said cavity having a top level substantially at the same elevation of said liquid outlet tube, a density indicator constructed of a float and a measuring stick integrally joined together such that when the float is submerged in said liquid, the measuring stick is emerged above said top level of the liquid, at least two positioning guides fixedly attached to said cylindrical housing adapted for guiding said measuring stick in a substantially upright position, and an optical sensor mounted on said cylindrical-shaped housing for sensing a position of said measuring stick.

17. An apparatus for on-line, real-time monitoring of a liquid density according to claim 16 further comprising a process controller for receiving a signal indicative of a density reading from said optical sensor and comparing said signal to a pre-set density value.

18. An apparatus for on-line, real-time monitoring of a liquid density according to claim 17 further comprising a process controller which stops a chemical process when said density reading obtained is outside an allowable range of said pre-set density value.

19. An apparatus for on-line, real-time monitoring of a liquid density according to claim 16, wherein said optical sensor comprises two pairs of optical beam senders and optical beam receivers for sensing a maximum allowable density value and a minimum allowable density value.

* * * * *